US008107730B2

(12) United States Patent
Kariv (10) Patent No.: US 8,107,730 B2
(45) Date of Patent: Jan. 31, 2012

(54) IMAGING SYSTEM SAG CORRECTION METHOD AND APPARATUS

(75) Inventor: Dov Kariv, Kfar Vradim (IL)

(73) Assignee: General Electric Company, Schenectady, NY (US)

( * ) Notice: Subject to any disclaimer, the term of this patent is extended or adjusted under 35 U.S.C. 154(b) by 848 days.

(21) Appl. No.: 12/186,125

(22) Filed: Aug. 5, 2008

(65) Prior Publication Data

US 2010/0034435 A1 Feb. 11, 2010

(51) Int. Cl.
*G06K 9/00* (2006.01)
(52) U.S. Cl. .......................................... 382/182
(58) Field of Classification Search .......... 324/300–322; 600/407–481; 382/128–134; 128/922; 250/455; 378/4–27
See application file for complete search history.

(56) References Cited

U.S. PATENT DOCUMENTS

| | | | | |
|---|---|---|---|---|
| 5,273,043 A * | 12/1993 | Ruike | ............................ | 600/436 |
| 5,448,996 A * | 9/1995 | Bellin et al. | ................... | 600/574 |
| 5,872,829 A | 2/1999 | Wischmann et al. | | |
| 6,496,558 B2 * | 12/2002 | Graumann | ....................... | 378/39 |
| 6,561,695 B2 * | 5/2003 | Proksa | ........................... | 378/207 |
| 6,895,105 B2 | 5/2005 | Wollenweber | | |
| 7,020,315 B2 | 3/2006 | Vaisburd et al. | | |
| 7,030,615 B2 * | 4/2006 | Gortler | .......................... | 324/318 |
| 7,170,972 B2 * | 1/2007 | Altman | ............................ | 378/62 |
| 7,233,002 B2 * | 6/2007 | Ohana et al. | ............. | 250/363.04 |
| 7,332,724 B2 * | 2/2008 | Hefetz et al. | .............. | 250/370.06 |
| 7,412,027 B2 * | 8/2008 | Yakubovsky et al. | ........... | 378/63 |
| 7,467,008 B2 * | 12/2008 | Vija | .............................. | 600/436 |
| 7,531,807 B2 * | 5/2009 | Hefetz | ..................... | 250/363.02 |
| 7,607,833 B2 * | 10/2009 | Marzendorfer | ............... | 378/209 |
| 7,677,802 B2 * | 3/2010 | Haras | ............................ | 378/209 |
| 7,693,565 B2 * | 4/2010 | Shai et al. | ..................... | 600/407 |
| 7,732,774 B2 * | 6/2010 | Majewski | ................. | 250/363.04 |
| 2007/0050908 A1 | 3/2007 | Kogan et al. | | |
| 2007/0053486 A1 | 3/2007 | Zelnik et al. | | |

\* cited by examiner

*Primary Examiner* — Dixomara Vargas
(74) *Attorney, Agent, or Firm* — Dean D. Small; The Small Patent Law Group (57) ABSTRACT

An apparatus for use with a single modality imaging system configured to generate uncorrected imaging data of a patient, the single modality imaging system includes two gamma cameras and a patient stretcher disposed between the two gamma cameras, the apparatus for compensating for downward stretcher deflection at the extended end of the patient stretcher that occurs during stretcher extension. The apparatus includes a single sag sensor for sensing the downward deflection of the patient stretcher, a subtracting device configured to generate a sag correction factors based on a baseline stretcher height and an input received from the sag sensor, and a compensator configured to modify at least a portion of the uncorrected imaging data to compensate for sag using the using the sag correction factor to generate a unified image.

21 Claims, 4 Drawing Sheets

IMAGING SYSTEM SAG CORRECTION METHOD AND APPARATUS

BACKGROUND OF THE INVENTION

This invention relates generally to medical imaging systems and more particularly to a method and system for compensating for misalignment of image data sets caused by patient stretcher deflection.

Medical imaging requires accurate and repeatable positioning of the patient for a scan and a table that facilitates minimizing attenuation of the gamma radiation. However, in medical imaging systems using, for example, a large field-of-view (FOV) gamma camera, the patient stretcher may experience sag when performing a whole-body Single Photon Emission Tomography (SPECT) scan. The sag condition may cause displacement of images acquired at different stretcher positions during the scanning procedure.

One known method of reducing patient stretcher sag is to provide a reinforced table such that the vertical alignment within the imaging system can be maintained. However, when a patient is imaged using a wide FOV imaging system the patient stretcher is extended to accommodate the axial length of imaging system. A reinforced table may still not be sufficient to eliminate patient stretcher sag when a larger patient is being imaged. While utilizing a reinforced table is an option, fabricating a table having the increased stiffness required to eliminate patient stretcher sag may be relatively expensive. Moreover, it is advantageous to make the patient stretcher as thin as possible so that the detectors may be as close to the patient when directly underneath the patient as the spatial resolution deteriorate with distance. Additionally, it is advantageous to make the patient stretcher as radiation transparent as possible so as to minimize its interference with the measurement. Commonly patient stretchers are made of thin structure of composite material.

Another known method for correcting table sag is utilized in a multi-modality imaging system. This method includes utilizing a plurality of sensors that are installed downstream from the first modality in the multi-modality imaging system. The plurality of sensors identify the stretcher sag that occurs between each imaging system in the dual-modality imaging system and at a point furthest downstream from where the stretcher is inserted into the dual-modality imaging system. While this method is effective for identifying stretcher sag in a dual-modality imaging system, using multiple sensors in a single modality imaging system may increase the cost of the overall single-modality imaging system without necessarily increasing the accuracy of the stretcher sag measurement and therefore may not improve the ability of the single-modality imaging systems to compensate for misalignment of image data sets caused by the stretcher deflection.

BRIEF DESCRIPTION OF THE INVENTION

In one embodiment, an apparatus for use with a single modality imaging system configured to generate uncorrected imaging data of a patient is provided. The apparatus includes two gamma cameras and a patient stretcher disposed between the gamma cameras, the apparatus for compensating for downward stretcher deflection at the extended end of the patient stretcher that occurs during stretcher extension. The apparatus includes a single stretcher sag sensor for sensing the downward deflection of the patient stretcher, a subtracting device configured to generate a sag correction factors based on a stretcher baseline height and an input received from the sag sensor, and a compensator configured to modify at least a portion of the uncorrected imaging data to compensate for sag using the using the sag correction factor to generate a unified image.

In another embodiment, a nuclear medicine imaging system is provided. The nuclear medicine imaging system includes a first gamma camera, a second gamma camera, and a patient stretcher disposed between the first and second gamma cameras. The nuclear medicine imaging system also includes a single sag sensor for sensing the downward deflection of the patient stretcher, a subtracting device configured to generate a sag correction factors based on a stretcher baseline height and an input received from the sag sensor, and a compensator configured to modify at least a portion of the uncorrected imaging data to compensate for stretcher sag using the using the sag correction factor.

In a further embodiment, a method for correcting imaging data acquired using a medical imaging system is provided. The medical imaging system includes a first gamma camera, a second gamma camera, and a patient stretcher disposed between the first and second gamma cameras. The method includes determining a baseline position of the patient stretcher to generate a baseline stretcher position, determining a downward stretcher deflection at an extended end of the patient stretcher that occurs during stretcher extension to generate a sag correction factor for each stretcher position during an imaging process, subtracting the sag correction factor from the baseline stretcher position, and modifying at least a portion of the uncorrected imaging data to generate a unified image.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular properly may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 1:
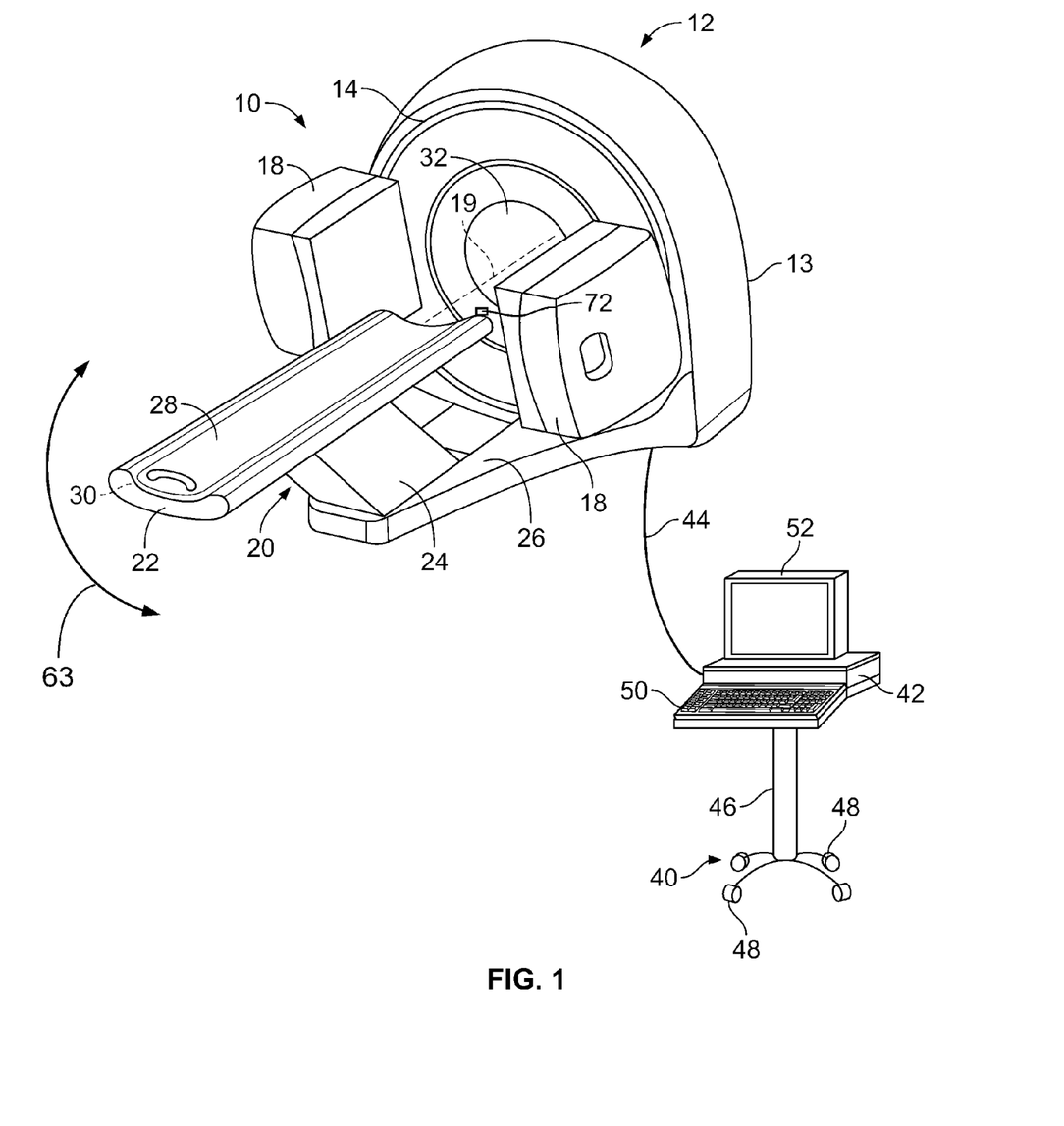
FIG. 1 is a perspective view of an exemplary nuclear medicine imaging system in accordance with an embodiment of the present invention.

Various embodiments of the invention provide a single-modality imaging system 10 as shown in FIG. 1. The single-modality imaging system 10 may be any type imaging system, for example, different types of medical imaging systems, such as a Positron Emission Tomography (PET), a Single Photon Emission Computed Tomography (SPECT), a Computed Tomography (CT), an ultrasound system, Magnetic Resonance Imaging (MRI) or any other system capable or generating tomographic images. Moreover, the various embodiments are not limited to medical imaging systems for imaging human subjects, but may include veterinary or non-medical systems for imaging non-human objects, or non-destructive testing systems (e.g. airport baggage systems) etc.

The single-modality imaging system 10 in the preferred embodiment is a nuclear medicine imaging system 10 that includes an integrated gantry 12 that further includes a stator 13, a rotor 14 oriented about a gantry central bore 32 that defines the patient imaging area. The rotor 14 is configured to support one or more nuclear medicine (NM) cameras 18, such as, but not limited to gamma cameras, SPECT detectors, and/or PET detectors. In the preferred embodiment, cameras 18 are large axial Field Of View (FOV) gamma detectors, for example having axial sensitive dimension of 15 to 50 cm. The rotor 14 is further configured to rotate axially about an examination axis 19. A patient table 20 may include a bed 22 slidingly coupled to a bed support system 24, which may be coupled directly to a floor or may be coupled to the gantry 12 through a base 26 coupled to gantry 12. The bed 22 may include a stretcher 28 slidingly coupled to an upper surface 30 of the bed 22. The patient table 20 is configured to facilitate ingress and egress of a patient (not shown) into an examination position that is substantially aligned with the examination axis 19. During an imaging scan, the patient table 20 is controlled to move the bed 22 and/or stretcher 28 axially into and out of the central bore 32. Additionally, the imaging system 10 includes a table motion controller 34 that is configured to facilitate up and down movement of the stretcher 28 so as to center different size patients in the center of bore 32 and to move the stretcher 28 through the central bore 32.

In the exemplary embodiment, the imaging system 10 also includes a scanner workstation 40 to operate and/or control of the various components of the imaging system 10. The scanner workstation 40 includes a computer 42 that is coupled to the gantry 12 via a wired link 44, for example, a wired cable. Alternatively, communication between the scanner workstation 40 and the gantry 12 may be provided via a wireless link. The scanner workstation 40 also includes a stand 46, that may be movable (e.g., on wheels 48) and that supports a user input, such as a keyboard 50. A display, such as, a monitor 52 (e.g., an acquisition console screen) is also provided. In operation, the scanner workstation 40 is configured to position and/or align the patient table 20 in at least one of an axial direction and a vertical or radial direction. Movement of the patient table 20 may be controlled with user commands provided at the user input 50 in a manual mode or may be controlled automatically, e.g. a programmed scan.

Figure 2A:
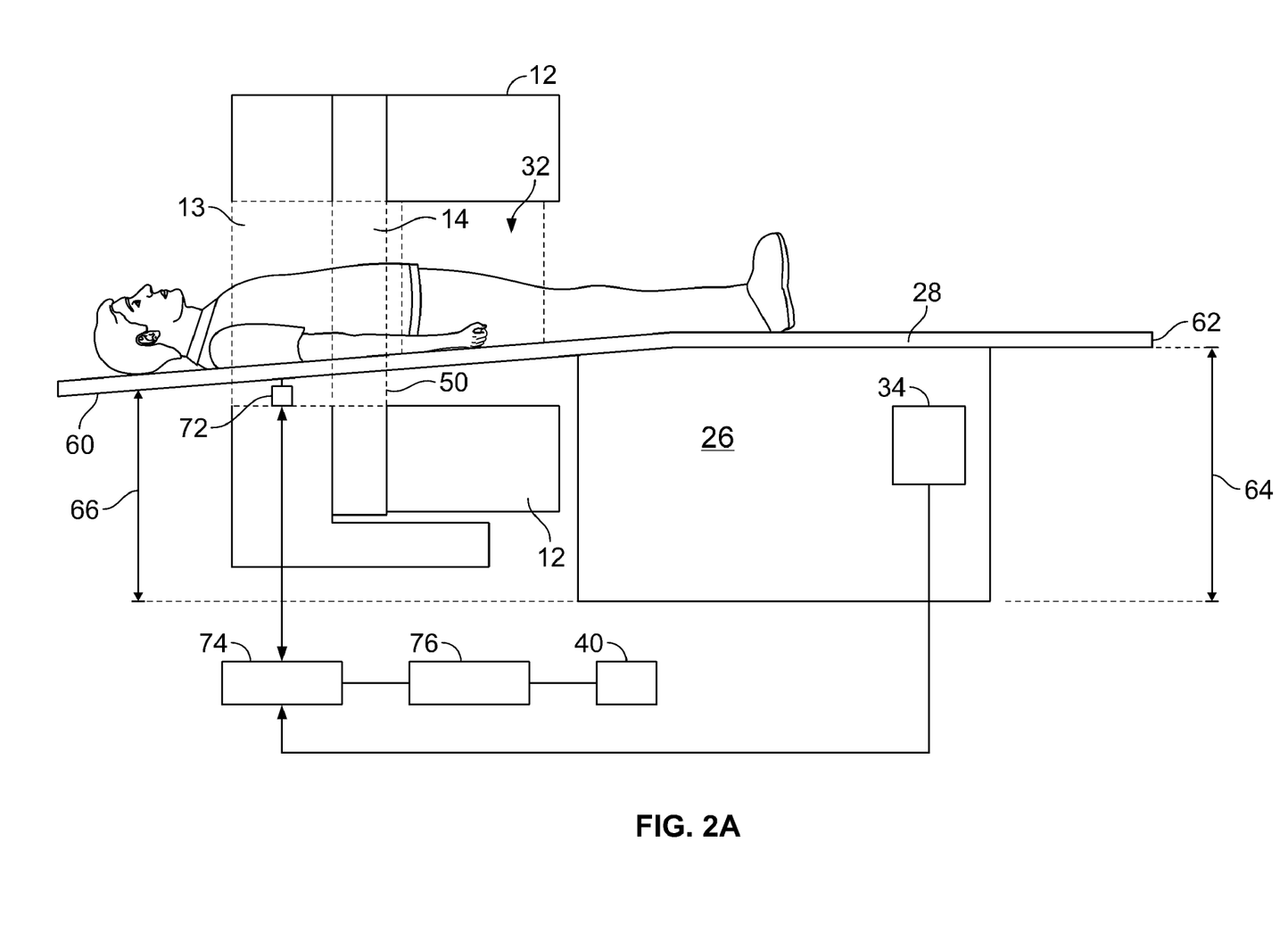
FIG. 2A is a side view of the imaging system shown in FIG. 1 in a first operational position.
Figure 2B:
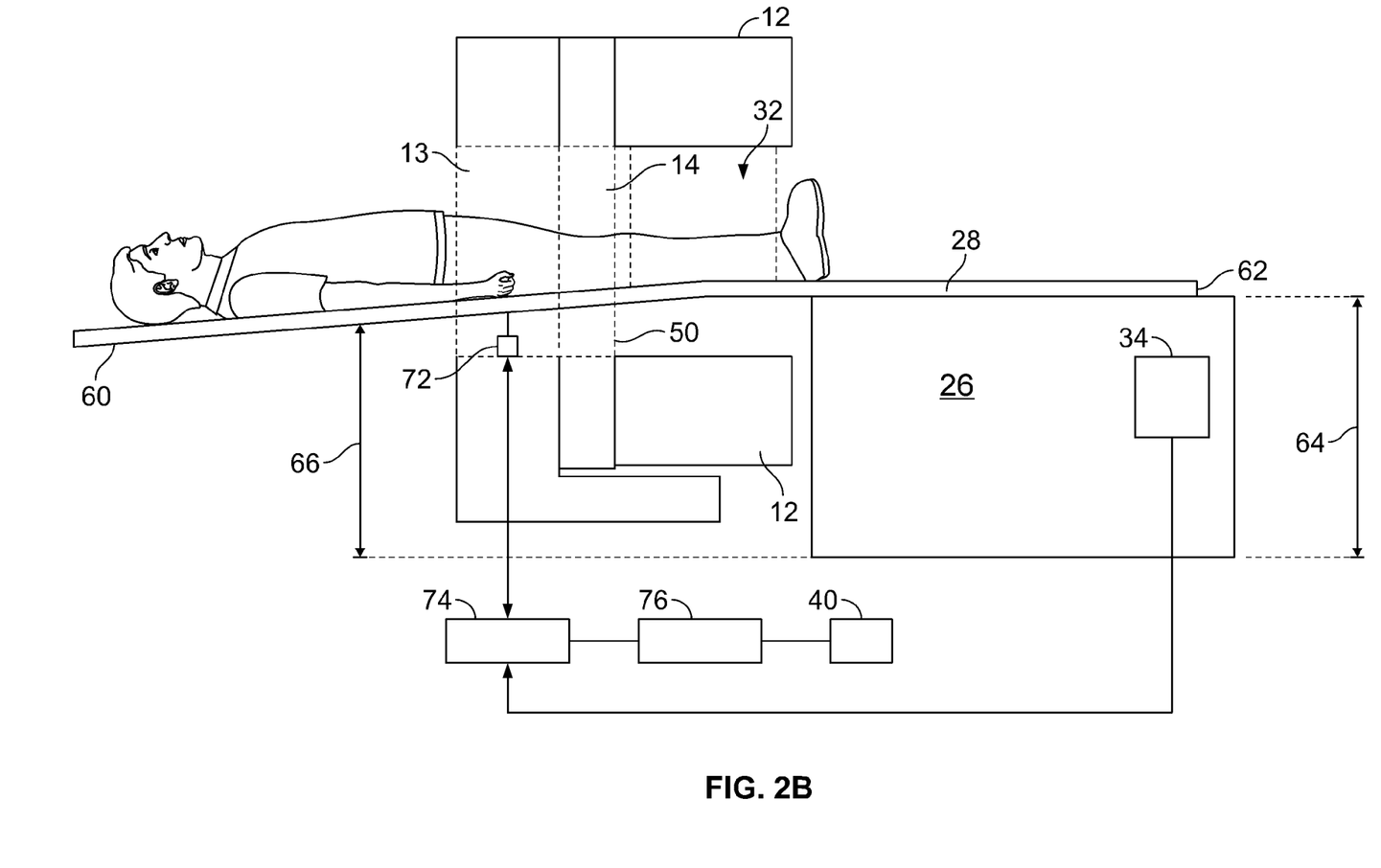
FIG. 2B is a side view of the imaging system shown in FIG. 1 in a second operational position.

FIG. 2A is a simplified schematic illustration of a portion of the exemplary imaging system 10 shown in FIG. 1 in a first operational position. FIG. 2B is a simplified schematic illustration of a portion of the exemplary imaging system 10 shown in FIG. 1 in a second operational position. As shown in FIGS. 2A and 2B, when the stretcher 28 is moved into and through an imaging area defined through the central bore 32 in a direction that is parallel to the examination axis 19, a first end 60 of the stretcher 28 passes through imaging area while a second end 62 of stretcher 28 remains secured to base 26. It should be appreciated from FIG. 2A that when stretcher 28 is extended as illustrated in FIG. 2B, the stretcher 28 tends to sag or deflect downward at the extended end 60. This is particularly the case when relatively heavy patients are supported by stretcher 28. Thus, because stretcher 28 deflects downward, when imaging data is acquired, the relative vertical position 63 of the stretcher 28 will be at a first height 64 and at least a portion of the patient being imaged will be at a second height 66. In the exemplary embodiment, the first and second heights 64 and 66 may be determined from any fixed position using a sensor as described in more detail below. For example, the first and second heights 64 and 66 may be determined from the same fixed position, e.g., a floor. Optionally, the first and second heights 64 and 66 may be determined from different fixed positions. Variable height 64 is accurately known from table motion controller 34, through use of sensors and/or motor encoders within table 26.

To compensate for the misalignment or sag of stretcher 28, in the exemplary embodiment, imaging system 10 also includes a stretcher sag sensor 72. In one embodiment, the stretcher sag sensor 72 is disposed adjacent the examination axis 19 and outside the imaging field of view (FOV). In the exemplary embodiment, the imaging system 10 includes only one single sag sensor 72 that is used to determine the amount or quantity of stretcher sag. In the exemplary embodiment, the stretcher sag sensor 72 is installed downstream from the gantry 12, on the stator 13, e.g. on the side of the gantry 12 where the patient stretcher 28 exits the gantry 12. The stretcher sag sensor 72 is used to determine the height of the stretcher 28. The stretcher sag sensor 72 can take any of various form including for example non-contact sensors such as: an ultrasonic sensor, a laser sensor, an acoustical sensor, an optical sensor, a light sensor, a magnetic sensor, or contact mechanical sensor and any other type of distance determining sensor known in the art.

In the exemplary embodiment, the stretcher sag is determined by comparing the physical output of the stretcher sag sensor 72 to the stretcher baseline height 64. As such, imaging system 10 also includes a subtracting device 74 that is configured to receive an output from the stretcher sag sensor 72 and perform a mathematical comparison between the stretcher sag sensor 72 output and the stretcher baseline height 64. The subtracting device 74 outputs a single value that reflects the difference in height between the stretcher 28 as measured at the baseline position and the height of the stretcher 28 exiting the gantry 12, e.g. the total stretcher sag. Moreover, using the output from the subtracting device 74, imaging system 10 can easily determine the relative positions of the cameras 18 to the stretcher 28. In the exemplary embodiment, the output from the subtracting device 74 is provided to a compensator 76. During operation, the compensator 76 is programmed to modify the uncorrected imaging data sets acquired from the imaging system 10 during the imaging process to compensate for the misalignment associated with heights 64 and 66, as describe in more detail below, and to generate at least one medical image using the modified uncorrected image data that does not include the affects of the misalignment. The medial image is then provided to workstation 40 for example for review by a system user.

Figure 3:
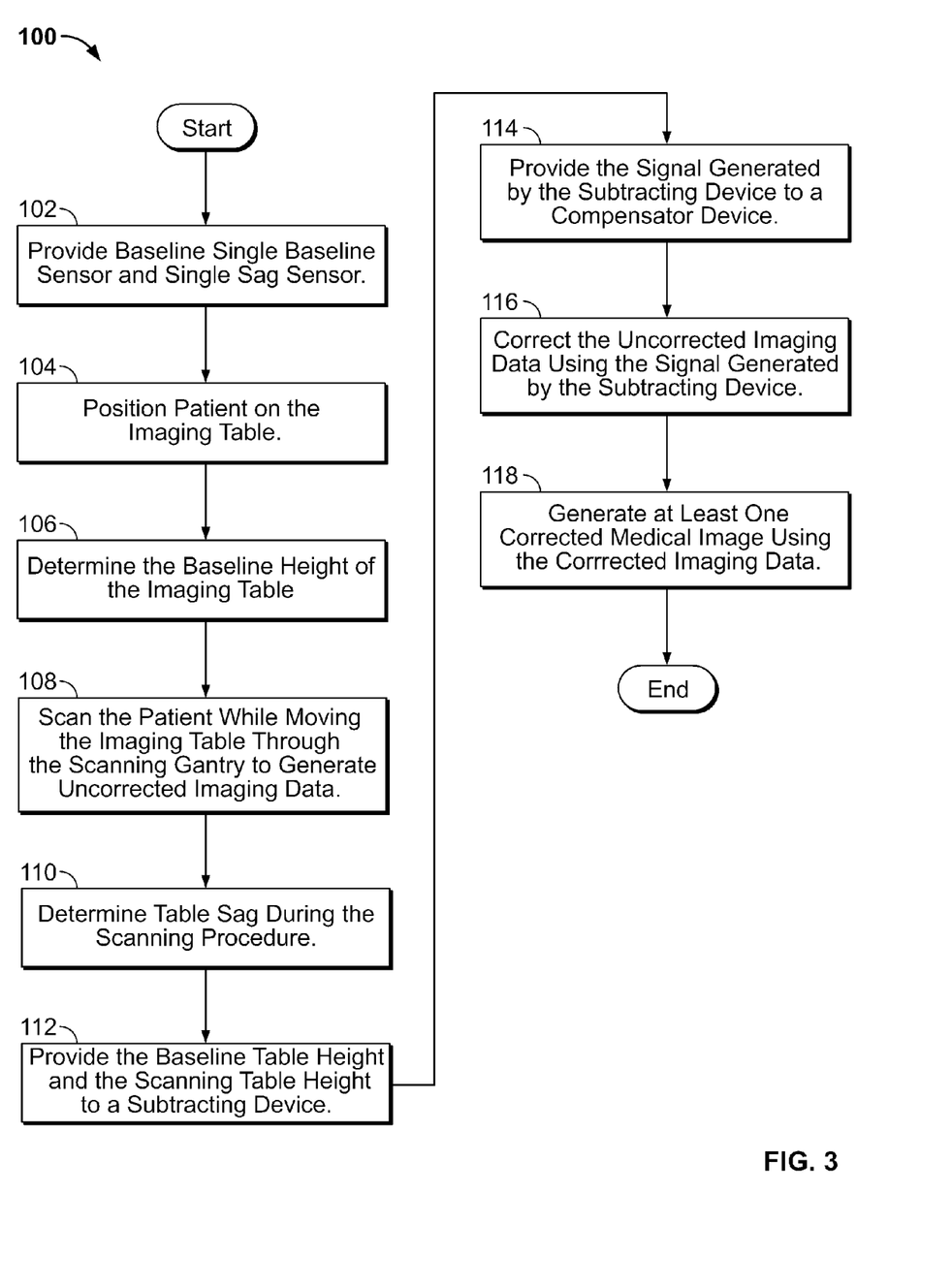
FIG. 3 is a flowchart illustrating an exemplary method for correcting imaging data using the imaging system shown in FIGS. 1 and 2.

FIG. 3 is a flowchart illustrating an exemplary method 100 for identifying and correcting imaging data caused by stretcher sag. At step 102 sensor 72 is activated. At step 104, a patient is positioned on stretcher 28 and the table 20 and the patient are positioned with respect to gantry 12. At step 106 the baseline height 64 of the stretcher 28 is determined. At step 108 the patient is then moved into or through gantry 12 until at least a portion of the stretcher 28 is positioned above the sag sensor 72 as shown in FIG. 2. It should apparent that during the imaging process, the patient is positioned on the stretcher 28 and the height of the stretcher 28 is determined at various stretcher positions during the scanning process using the sensor 72. The height of the stretcher 28, including the patient, prior to being inserted into the gantry 12 is referred to as the baseline height 64. The stretcher 28 is then at least partially inserted into the gantry 12 to perform patient imaging. As shown in FIG. 2, as the patient is moved through the gantry 12 and exits from gantry 12, the sensor 72 determines the stretcher sag at step 110. At step 112, the signal generated using sensor 72 and the baseline height 64 are provided to the subtracting device 74 to generate a sag correction factor. In the exemplary embodiment, the sag correction factor is the difference between the input received from the stretcher sag sensor 72 and the baseline height 64. At step 114, the signal generated using the subtracting device 74, e.g. the sag correction factor, is provided to the compensator 76. At step 116, the compensator 76 modifies the uncorrected imaging data sets acquired from the imaging system 10 based on the signal received from the subtracting device 74 to compensate for the misalignment associated with heights 64 and 66. For example, the assuming that each imaging slice has X, Y, and Z coordinates for each pixel in the acquired imaging slices, where X is defined as the vertical distance between the stretcher 28 and a fixed position and the change in the vertical distance is defined as the stretcher sag, the sag correction factor represents a value that the stretcher 28 has moved or deflected in the vertical or X axis during the imaging process. The imaging data is then corrected by modifying the data in the X direction using the sag correction factor. At step 118, the workstation 40 is programmed to generate at least one medical image using the modified uncorrected image data that does not include the affects of the misalignment.

At least one technical effect of the methods and apparatus described herein provides the ability to measure stretcher sag for each partial medical image or slice to generate a corrected medical image using a plurality of corrected medical images or slices that are each corrected to compensate for stretcher sag. Moreover, the methods may be used with a single modality imaging system including a gamma camera having a relatively large FOV, e.g., greater than approximately 50 centimeters. During operation, the method and apparatus described herein may be used when performing a "whole body" single photon emission tomography (SPECT) scanning procedure to determine the height of the patient stretcher, the effect of the sag on the displacement of images taken at different bed positions, and to correct the imaging data to compensate for the stretcher sag to produce a whole body image with reduced distortions and/or blurring. Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only-Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The method described herein may be embodied as a set of instructions on a computer. The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly-required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While the invention has been described in terms of various specific embodiments, those skilled in the art will recognize that the invention can be practiced with modification within the spirit and scope of the claims.

What is claimed is:

1. An apparatus for use with a single modality imaging system configured to generate uncorrected imaging data of a patient, the single modality imaging system includes at least one gamma camera and a patient stretcher disposed between the two gamma cameras, the apparatus comprising:
    a single sag sensor for sensing the downward deflection of the patient stretcher;
    a subtracting device configured to generate a sag correction factors based on a stretcher baseline height and an input received from the sag sensor; and
    a compensator configured to modify at least a portion of the uncorrected imaging data to compensate for sag using the using the sag correction factor to generate a unified image.

2. An apparatus in accordance with claim 1 wherein the single sag sensor is mounted on an imaging system stator.

3. An apparatus in accordance with claim 1 wherein the gamma camera has a field of view that is greater than approximately 15 centimeters.

4. An apparatus in accordance with claim 1 wherein the stretcher baseline height represents a height of the patient stretcher including the patient.

5. An apparatus in accordance with claim 1 wherein the sag sensor is positioned downstream from the imaging system gantry proximate to a distal end of the gamma camera field of view (FOV).

6. An apparatus in accordance with claim 1 wherein the uncorrected imaging data includes a plurality of slices, the subtracting device is configured to generate a sag correction factor for each slice, and the compensator is configured to modify each slice compensate for stretcher sag using the using the sag correction factors.

7. An apparatus in accordance with claim 1 wherein the sag sensor comprises at least one of an ultrasonic sensor, a laser sensor, an acoustical sensor, an optical sensor, a light sensor, and a magnetic sensor.

8. A nuclear medicine imaging system comprising:
    at least a first gamma camera;
    a patient stretcher disposed between the first gamma camera;
    a single sag sensor for sensing the downward deflection of the patient stretcher;
    a subtracting device configured to generate a sag correction factors based on a stretcher baseline height and an input received from the sag sensor; and
    a compensator configured to modify at least a portion of the uncorrected imaging data to compensate for stretcher sag using the using the sag correction factor.

9. A nuclear medicine imaging system in accordance with claim 8 wherein the gamma camera has a field of view that is greater than approximately 15 centimeters.

10. A nuclear medicine imaging system in accordance with claim 8 wherein the stretcher baseline height represents a height of the patient stretcher including the patient.

11. A nuclear medicine imaging system in accordance with claim 8 wherein the sag sensor is positioned downstream from the imaging system gantry proximate to a distal end of the gamma camera field of view (FOV).

12. A nuclear medicine imaging system in accordance with claim 8 wherein the uncorrected imaging data includes a plurality of slices, the subtracting device is configured to generate a sag correction factor for each slice, and the compensator is configured to modify each slice compensate for stretcher sag using the using the sag correction factors.

13. A nuclear medicine imaging system in accordance with claim 8 wherein the sag sensor comprises at least one of an ultrasonic sensor, a laser sensor, an acoustical sensor, an optical sensor, a light sensor, and a magnetic sensor.

14. A method for correcting imaging data acquired using a medical imaging system, the medical imaging system including at least a first gamma camera, and a patient stretcher disposed between the first gamma camera, the method comprises:
    determining a baseline position of the patient stretcher to generate a baseline stretcher position;
    determining a downward stretcher deflection that occurs during stretcher extension to generate a sag correction factor for each stretcher position during an imaging process;
    subtracting the sag correction factor from the baseline stretcher position for each stretcher position; and
    modifying at least a portion of the uncorrected imaging data to generate a three-dimensional medical image.

15. A method in accordance with claim 14 further comprising modifying at least a portion of the uncorrected imaging data to generate a unified three-dimensional nuclear medicine medical image.

16. A method in accordance with claim 14 further comprising acquiring the uncorrected imaging data using a gamma camera having a field-of-view that is at least 15 centimeters.

17. A method in accordance with claim 14 further comprising determining a baseline position of the patient stretcher including the patient to generate a baseline stretcher position.

18. A method in accordance with claim 14 further comprising positioning positioning the sag sensor downstream from the system gantry proximate to a distal end of the gamma camera field of view (FOV).

19. A method in accordance with claim 14 further comprising:
   generating uncorrected imaging data that includes a plurality of slices;
   generating a sag correction factor for each slice; and
   generating a single three-dimensional image using the plurality of sag correction factors.

20. A method in accordance with claim 14 further comprising using at least one of an ultrasonic sensor, a laser sensor, an acoustical sensor, an optical sensor, a light sensor, and a magnetic sensor to generate a signal that represents stretcher sag.

21. A method in accordance with claim 14 further comprising:
   generating uncorrected imaging data at a first and a second stretcher position;
   correcting the uncorrected imaging data at the first and second stretcher positions using the sag correction factor to generate a first corrected image and a second corrected image; and
   generating a composite image from the first and second corrected images such that the image discontinuity at the transition from image acquired in first stretcher position and second stretcher position is minimized.

* * * * *

UNITED STATES PATENT AND TRADEMARK OFFICE
CERTIFICATE OF CORRECTION

| | | |
|---|---|---|
| PATENT NO. | : 8,107,730 B2 | |
| APPLICATION NO. | : 12/186125 | |
| DATED | : January 31, 2012 | |
| INVENTOR(S) | : Kariv | |

It is certified that error appears in the above-identified patent and that said Letters Patent is hereby corrected as shown below:

On the Face Page, in Field (57), under "ABSTRACT", in Column 2, Line 13-14, delete "using the using the" and insert -- using the --, therefor.

In Column 1, Lines 15-16, delete "Single Photon Emission Tomography (SPECT)" and insert -- Single Photon Emission Computed Tomography (SPECT) --, therefor.

In Column 2, Line 2, delete "using the using the" and insert -- using the --, therefor.

In Column 2, Lines 14-15, delete "using the using the" and insert -- using the --, therefor.

In Column 3, Line 4, delete "properly" and insert -- property --, therefor.

In Column 5, Line 57, delete "single photon emission tomography (SPECT)" and insert -- single photon emission computed tomography (SPECT) --, therefor.

In Column 7, Lines 49-50, in Claim 1, delete "using the using the" and insert -- using the --, therefor.

In Column 8, Lines 1-2, in Claim 6, delete "using the using the" and insert -- using the --, therefor.

In Column 8, Line 18, in Claim 8, delete "using the using the" and insert -- using the --, therefor.

In Column 8, Line 34, in Claim 12, delete "using the using the" and insert -- using the --, therefor.

Signed and Sealed this
Eighteenth Day of September, 2012

David J. Kappos
*Director of the United States Patent and Trademark Office*

In Column 8, Line 65, in Claim 18, delete "positioning positioning" and insert -- positioning --, therefor.